United States Patent
Kley et al.

(10) Patent No.: US 8,791,260 B2
(45) Date of Patent: Jul. 29, 2014

(54) PROCESS FOR THE PREPARATION OF ACYLGUANIDINES AND ACYLTHIOUREAS

(71) Applicants: Joerg Kley, Mittelbiberach (DE); Daniel Haerle, Oberstadion-Moosbeuren (DE); Guenter Linz, Mittelbiberach (DE); Sandra Stehle, Hochdorf (DE)

(72) Inventors: Joerg Kley, Mittelbiberach (DE); Daniel Haerle, Oberstadion-Moosbeuren (DE); Guenter Linz, Mittelbiberach (DE); Sandra Stehle, Hochdorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/047,043

(22) Filed: Oct. 7, 2013

(65) Prior Publication Data
US 2014/0039189 A1 Feb. 6, 2014

Related U.S. Application Data

(62) Division of application No. 13/662,792, filed on Oct. 29, 2012, now abandoned.

(30) Foreign Application Priority Data

Nov. 2, 2011 (EP) .................................... 11187566

(51) Int. Cl.
| | | |
|---|---|---|
| *C07D 403/12* | (2006.01) | |
| *C07D 241/06* | (2006.01) | |
| *C07D 241/40* | (2006.01) | |
| *C07D 241/44* | (2006.01) | |
| *C07C 233/11* | (2006.01) | |
| *C07C 233/48* | (2006.01) | |
| *C07D 241/28* | (2006.01) | |
| *C07C 231/14* | (2006.01) | |
| *C07D 233/48* | (2006.01) | |

(52) U.S. Cl.
CPC ............ *C07C 231/14* (2013.01); *C07D 241/28* (2013.01); *C07C 233/11* (2013.01); *C07D 241/06* (2013.01); *C07D 241/44* (2013.01); *C07D 241/40* (2013.01); *C07D 233/48* (2013.01); *C07D 403/12* (2013.01)
USPC ........ 544/355; 544/405; 544/407; 548/332.5; 560/37

(58) Field of Classification Search
None
See application file for complete search history.

(56) References Cited

U.S. PATENT DOCUMENTS 3,953,476 A 4/1976 Cragoe, Jr. et al.

FOREIGN PATENT DOCUMENTS

| GB | 1214408 A | 12/1970 |
| GB | 1214409 | * 12/1970 |
| GB | 1214409 A | 12/1970 |
| WO | 2008135557 A1 | 11/2008 |
| WO | 2009138378 A1 | 11/2009 |
| WO | 2013003386 A1 | 1/2013 |
| WO | 2013003444 A1 | 1/2013 |

OTHER PUBLICATIONS

Non-coordinating_anion, 2014, http://en.wikipedia.org/wiki/Non-coordinating.anion.*
Non-coordinating_anion-date, 2014, http://web.archive.org/web/*/http://en.wikipedia.org/wiki/Non-coordinating_anion.*
Laeckmann et al., Bioorganic&Medicinal Chemistry, 10, 2002, 1793-1804.*
Berge, Stephen, M., et al; Review Article: Pharmaceutical Salts; Journal of Pharmaceutical Sciences (1977) vol. 66, No. 1 pp. 1-19.
European Search Report for EP 11187553 Date of Completion of the Search Feb. 10, 2012.
European Search Report for EP 11187566 Date of Completion of the Search May 10, 2012.
Hirsch, Andrew, J., et al; Design, Synthesis, and Structure-Activity relationships of Novel 2-Substituted Pyrazinoylguanidine Epithlial Sodium Channel Blockers: Drugs for Cystic Fibrosis and Chronic Brochitis; Journal of Medicinal Chemistry (2006) vol. 49, No. 14 pp. 4098-4115.
Li, Jack, H., et al; Stereoselective Blockade of Amphibian Epithelial Sodium Channels by Amiloride Analogs; The Journal of Pharmacology and Experimental Therapeutics (1993) vol. 267, No. 3 pp. 1081-1084.
Rogister, Francoise, et al; Novel Inhibitors of the Sodium-Calcium Exchanger: Benzene Ring Analogues of N-Guanidino Substituted Amiloride Derivatives; European Journal of Medicinal Chemistry (2001) vol. 36, No. 7-8 pp. 597-614.
Shepard, Kenneth, L. et al; 3,5-Diamino-6-Chloropyrazinecarboxylic Acid "Active Esters" and Their Reactions (1); Tetrahedron Letters (1969) vol. 54 pp. 4757-4760.
Short, James, H. et al., Sympathetic Nervous System Blocking Agents. Derivates of Guanidine and Related Compounds; Journal of Medicinal Chemistry (1963) vol. 6 pp. 275-283.
U.S. Appl. No. 13/662,791, filed Oct. 29, 2012, InventorArmin Heckel.

(Continued)

*Primary Examiner* — Sun Jae Yoo
(74) *Attorney, Agent, or Firm* — Michael P. Morris; Edward S. Lazer

(57) ABSTRACT

The present invention relates to a novel process for the preparation of compounds of general formula (I)

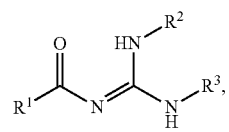

(I)

and the salts thereof, particularly the physiologically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

2 Claims, No Drawings

(56) References Cited

OTHER PUBLICATIONS

U.S. Appl. No. 13/662,792, filed Oct. 29, 2012, Inventor Joerg Kley.
European Search Report for EP 11194687 Date of Completion of the Search Mar. 7, 2012.
Laeckmann, D. et al., "Synthesis and Biological Evaluation of Aroylguanidines Related to Amilorade as Inhibitors of the Human Platelet Na+/H+Exchanger". Bioorganic Medical Chemistry 2002, 1793-1804.
Shepard, K.L., et al., Activated Esters of Substituted Pyrazinecarboxylic Acids (1). Journal of Heterocyclic Chemistry, 1976, 1219-1224.
Woodman, D.J., "N-t-Butyl-acyloxycrotonamides". Journal of Organic Chemistry, 1970, p. 83-87.
Alberola, A., et al., "The Reactions of 3-Unsubstituted Isoxazolium Salts with 1,2-Dinucleophiles, Synthesis of 4-Funtionalized 3-Aminoisoxazoles and 3-Aminopyrazoles". Synthesis 1988, 203-207.
International Search Report, Form PCT/ISR/210, for corresponding application PCT/EP2012/076101 date of mailing Jan. 22, 2013.

\* cited by examiner

PROCESS FOR THE PREPARATION OF ACYLGUANIDINES AND ACYLTHIOUREAS

The present invention relates to a novel process for the preparation of compounds of general formula (I)

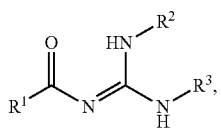
(I)

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways, comprising intermediates of general formula (III) and optionally (II) and/or (IV).

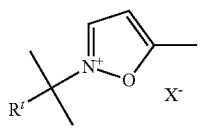
(II)

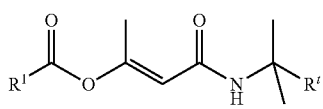
(III)

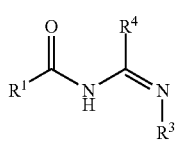
(IV)

BACKGROUND TO THE INVENTION

Compounds of formula (I) are known from the prior art as active substances for example for the treatment of diseases of the lungs and airways (*J. Med. Chem.* 49 (2006) 4098-4115). Processes for preparing compounds of formula (I) from compounds of formula (III) with $R^t$=methyl (Laeckmann, D. et al. Bioorg., Med. Chem. 10 (2002) 1793-1804) or from compounds of formula (IV) (*J. Med. Chem.* 49 (2006) 4098-4115) are known from the prior art. 2-Tert-butyl-5-methyl-1,2-oxazol-2-ium perchlorate (tert-butyl-methylisoxazolium perchlorate), also referred to as "Woodward's reagent L" is known from the prior art as an intermediate for the synthesis of compounds of formula (III) (Laeckmann, D. et al. Bioorg. Med. Chem. 10 (2002) 1793-1804). Due to the known oxidizing properties of the perchlorate ion, the use of tert-butyl-methylisoxazolium perchlorate may constitute a substantial hazard, especially when applied in larger scale. The "Recommendations on the transport of dangerous goods; Manual of Tests and Criteria (United Nations, 5th revised ed. 2010; appendix 6, page 440, Table A6.1)" list the perchlorate moiety as a group indicating explosive properties in organic materials. No salts of the 2-tert-butyl-5-methyl-1,2-oxazol-2-ium ion other than the perchlorate are known from the literature.

The preparation of compounds of formula (IV) from compounds of formula (III) is known from the prior art (Shepard, K. L. et al. J. Heterocyclic Chem. 13 (1976) 1219-1224). The preparation of compounds of formula (IV) from compounds of formula (V)

$$R^1\text{—COOH} \quad (V)$$

without generating compounds of formula (III) as intermediates is described in WO2009074575. The reaction described therein requires the coupling reagent O-(7-azabenzotriazol-1-yl)-N,N,N',N'-tetramethyluronium hexafluorophosphate (HATU) which is regarded as a potential explosive.

The problem of the present invention is to provide a process, which avoids the use of highly hazardous intermediates or reagents, for preparing compounds of formula (I).

Especially the problem of the present invention is to provide a process, which avoids the use of highly hazardous intermediates, for preparing compounds of formula (III) or (IV).

Especially the problem of the present invention is to provide a process for preparing compounds of formula (I) without the use of 2-tert-butyl-5-methyl-1,2-oxazol-2-ium perchlorate, other perchlorate salts, perchloric acid, HATU, O-(Benzotriazol-1-yl)-N,N,N',N'-tetramethyluronium tetrafluoroborate (TBTU) or other reagents based on 1-hydroxy-7-azabenzotriazole (HOAt) or 1-hydroxybenzotriazole (HOBT) or hydrogen sulphide. In order to avoid highly hazardous intermediates the exothermic decomposition energy of reagents and intermediates applied in the process should be less than 2000 J/g and the onset of exothermic decomposition (if applicable) should be above 180° C. (For comparison: Differential Scanning calorimetry data (Closed gold vessel) for 2-tert-butyl-5-methyl-1,2-oxazol-2-ium perchlorate ("Woodward's reagent L"): Exothermic event of $\Delta H$=4395 J/g and $T_{onset}$=158° C.)

DESCRIPTION OF THE INVENTION

The present invention solves the above-mentioned problems by the method of synthesis described hereinafter.

The invention thus relates to a process for the preparation of compounds of general formula (I)

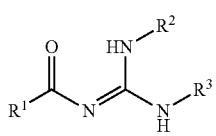
(I)

optionally in the form of the tautomers thereof, and optionally the acid addition salts thereof, wherein
R$^1$ denotes a group of formula (i),

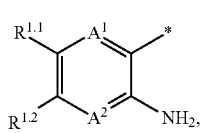
(i)

wherein
A$^1$ and A$^2$ independently from each other denote N or CH;
R$^{1.1}$ denotes hydrogen or a group selected from among chloro, bromo and methyl, $R^{1.2}$ denotes hydrogen or a group selected from among amino, $C_{1-3}$-alkyl-NH—, $(C_{1-3}$-alkyl$)_2$N— and methyl, or $R^{1.1}$ and $R^{1.2}$ together form an annelated benzo ring;

$R^2$ denotes hydrogen or a group selected from among $C_{1-6}$-alkyl, $C_{6-10}$-aryl-$C_{1-6}$-alkyl-, heterocyclyl and heterocyclyl-$CH_2$—, or $R^2$ denotes a group of formula (ii) including the pure enantiomers and/or a mixture thereof

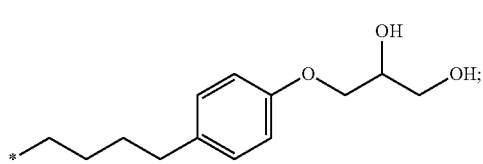

(ii)

or $R^2$ denotes, with the provisio that $A^1$ and $A^2$ denote N, a group of formula (iii),

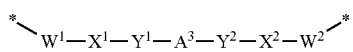

(iii)

wherein $W^1$ and $W^2$ are independently selected from among a bond or $C_{1-8}$-alkylene;

$X^1$ and $X^2$ are independently selected from among a 4- to 14-membered heterocyclic group;

$Y^1$ and $Y^2$ are independently selected from among a bond, $C_{1-8}$-alkylene and —$C_{1-8}$-alkylamino-;

$A^3$ is selected from the group consisting of a $C_{6-15}$-membered aromatic carbocyclic group, —$CONR^5$—(C_{1-8}$-alkylene)-$NR^5CO$—, —CO—($C_{1-8}$-alkylene)-CO—, —CO—($C_{2-8}$-alkenylene)-CO—, —(CO)—, —CO—($C_{1-8}$-alkylene)-Z—($C_{1-8}$-alkylene)-CO—, —CO—($C_{1-8}$-alkylene)-Z—CO—, —CO—Z—CO—, —CO—$NR^5$—($C_{1-8}$-alkylene)-Z—($C_{1-8}$-alkylene)-$NR^5$—CO—, —CO—$NR^5$—($C_{1-8}$-alkylene)-Z—$NR^5$—CO—, —CO—$NR^5$—Z—$NR^5$—CO—, $C_{3-15}$-carbocyclic group and a 4- to 14-membered heterocyclic group;

Z is selected from among $C_{6-15}$-membered aromatic carbocyclic group, $C_{3-15}$-carbocyclic group and a 4- to 14-membered heterocyclic group;

$R^5$ is hydrogen or $C_{1-8}$-alkyl;

$R^3$ denotes hydrogen or methyl or $R^2$ and $R^3$ together denote —$CH_2$—$CH_2$— or —$CH_2$—$CH_2$—$CH_2$—, characterised in that the process comprises reaction steps (D) and (F), with the provisio that $R^2$ and $R^3$ together must not denote ethylene or propylene, wherein (D) is the reaction of a compound of formula (III) with a compound of formula (VI)

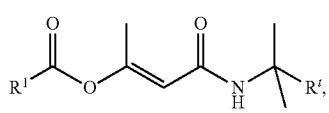

(III)

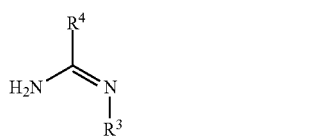

(VI)

wherein $R'$ denotes $C_{1-4}$-alkyl;

$R^4$ denotes a group selected from among $C_{1-4}$-alkylthio, 1-pyrazolyl, 1-imidazolyl and 1,2,4-triazol-1-yl, each optionally substituted by one or two methyl groups, to form a compound of formula (IV)

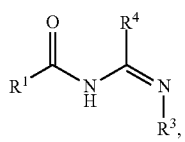

(IV)

and (F) is the reaction of a compound of formula (IV) with a compound of formula (VII)

(VII)

while steps (D) and (F) take place successively in the order specified, or characterised in that the process comprises reaction step (E), wherein (E) is the reaction of a compound of formula (III) with a compound of formula (VIII)

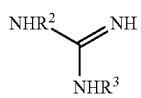

(VIII)

Preferred is a process for the preparation of a compound of formula (I)

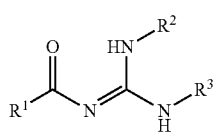

(I)

optionally in the form of the tautomers thereof, and optionally the acid addition salts thereof, wherein the process comprises reaction steps (B), (D) and (F), wherein (B) is the reaction of a compound of formula (II)

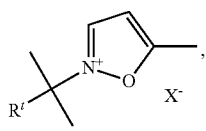
(II)

wherein
X⁻ denotes a group selected from among PF₆⁻, BF₄⁻, SbF₆⁻, phenylsulphonate, p-toluenesulphonate, HSO₄⁻, (SO₄²⁻)/2, FSO₃⁻ and F₃CSO₃⁻ and
R$^t$ denotes $C_{1-4}$-alkyl
with a compound of formula (V)

$$R^1\text{—COOH} \quad (V)$$

in the presence of a base,
to form a compound of formula (III)

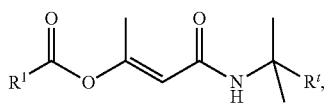
(III)

wherein
R$^t$ denotes $C_{1-4}$-alkyl;
(D) is the reaction of a compound of formula (III) with a compound of formula (VI)

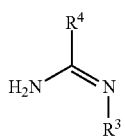
(VI)

wherein
R⁴ denotes a group selected from among $C_{1-4}$-alkylthio, 1-pyrazolyl, 1-imidazolyl and 1,2,4-triazol-1-yl, each optionally substituted by one or two methyl groups
to form a compound of formula (IV)

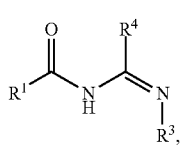
(IV)

and
(F) is the reaction of a compound of formula (IV) with a compound of formula (VII)

(VII)

while steps (B), (D) and (F) take place successively in the order specified,
or wherein the process comprises reaction steps (B) and (E), wherein
(E) is the reaction of a compound of formula (III) with a compound of formula (VIII)

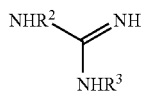
(VIII)

while steps (B) and (E) take place successively in the order specified.
or
wherein the process comprises reaction steps (C), (D) and (F), wherein
(C) is the reaction of a tertiary alcohol selected from tert-butanol, 2-methyl-2-butanol, 2-methyl-2-pentanol, 2-methyl-2-hexanol, 2,3-dimethyl-2-butanol and 2,4-dimethyl-2-pentanol;
and
5-methyl-1,2-oxazole
in the presence of an acid of formula XH
and a compound of formula (V) without isolation of a compound of formula (II) to form a compound of formula (III)
wherein
XH denotes an acid selected from among HPF₆, HBF₄, HSbF₆, phenylsulphonic acid, p-toluenesulphonic acid, H₂SO₄, (H₂SO₄)/2, F₃CCOOH, FSO₃H, and F₃CSO₃H;
R$^t$ denotes $C_{1-4}$-alkyl
or
wherein the process comprises reaction steps (C) and (E),
while steps (C) and (E) take place successively in the order specified.
A further embodiment of the current invention is a process for the preparation of compounds of general formula (III)
optionally in the form of the tautomers thereof, and optionally the acid addition salts thereof,
characterised in that the process comprises reaction steps (B) or (C),
wherein
(B) is the reaction of a compound of formula (II)

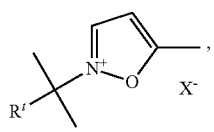
(II)

wherein
X⁻ denotes a group selected from among PF₆⁻, BF₄⁻, SbF₆⁻, phenylsulphonate, p-toluenesulphonate, HSO₄⁻, (SO₄²⁻)/2, FSO₃⁻ and F₃CSO₃⁻;
R$^t$ denotes $C_{1-4}$-alkyl; preferably methyl,
with a compound of formula (V)

$$R^1\text{—COOH} \quad (V)$$

in the presence of a base,
to form a compound of formula (III)

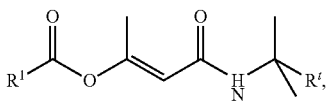

(III)

wherein
R¹ denotes a group of formula (i),

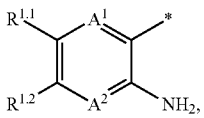

(i)

wherein
A¹ and A² independently from each other denote N or CH;
R$^{1.1}$ denotes hydrogen or a group selected from among chloro, bromo and methyl,
R$^{1.2}$ denotes hydrogen or a group selected from among amino, $C_{1-3}$-alkyl-NH—, $(C_{1-3}$-alkyl$)_2$N— and methyl,
or
R$^{1.1}$ and R$^{1.2}$ together form an annelated benzo ring;
R$^t$ denotes $C_{1-4}$-alkyl;
and
(C) is the reaction of a tertiary alcohol selected from tert-butanol, 2-methyl-2-butanol, 2-methyl-2-pentanol, 2-methyl-2-hexanol, 2,3-dimethyl-2-butanol and 2,4-dimethyl-2-pentanol;
and
5-methyl-1,2-oxazole
in the presence of an acid of formula XH
and a compound of formula (V) without isolation of a compound of formula (II) to form a compound of formula (III)
wherein
XH denotes an acid selected from among HPF₆, HBF₄, HSbF₆, phenylsulphonic acid, p-toluenesulphonic acid, H₂SO₄, (H₂SO₄)/2, F₃CCOOH, FSO₃H and F₃CSO₃H;
Preferably the process for the preparation of compounds of general formula (III),
wherein
R$^t$ denotes methyl or ethyl, particularly preferred ethyl,
comprises reaction step (C).
Preferably the process for the preparation of compounds of general formula (III),

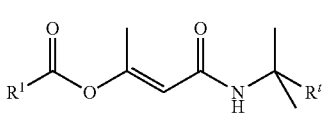

(III)

optionally in the form of the tautomers thereof, and optionally the acid addition salts thereof,
wherein
R¹ denotes a group of formula (i),

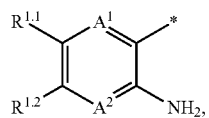

(i)

wherein
A¹ and A² independently from each other denote N or CH;
R$^{1.1}$ denotes hydrogen or a group selected from among chloro, bromo and methyl,
R$^{1.2}$ denotes hydrogen or a group selected from among amino, $C_{1-3}$-alkyl-NH—, $(C_{1-3}$-alkyl$)_2$N— and methyl;
R$^t$ denotes $C_{1-4}$-alkyl;
comprises reaction steps (A) and (B),
wherein
(A) is the reaction of a tertiary alcohol selected from among tert-butanol and 2-methyl-2-butanol, and 5-methyl-1,2-oxazole with an acid of formula XH to form a compound of formula (II)

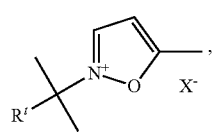

(II)

wherein
R$^t$ denotes methyl or ethyl; preferably methyl,
X⁻ denotes a group selected from among PF₆⁻, BF₄⁻, SbF₆⁻, phenylsulphonate, p-toluenesulphonate, HSO₄⁻, (SO₄²⁻)/2, FSO₃⁻, and F₃CSO₃⁻;
XH denotes the respective conjugate acid of X⁻;
while steps (A) and (B) take place successively in the order specified.
The invention further relates to a process for the preparation of compounds of general formula (II),

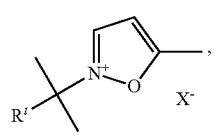

(II)

wherein
R$^t$ denotes $C_{1-4}$-alkyl;
X⁻ denotes a group selected from among PF₆⁻, BF₄⁻, SbF₆⁻, phenylsulphonate, p-toluenesulphonate, HSO₄⁻, (SO₄²⁻)/2, FSO₃⁻, and F₃CSO₃⁻.
wherein the process comprises reaction step (A),
wherein
(A) is the reaction of a tertiary alcohol selected from among tert-butanol, 2-methyl-2-butanol, 2-methyl-2-pentanol, 2-methyl-2-hexanol, 2,3-dimethyl-2-butanol and 2,4-dimethyl-2-pentanol
and 5-methyl-1,2-oxazole
with an acid of formula XH,
preferred is the reaction of tert-butanol or 2-methyl-2-butanol
and 5-methyl-1,2-oxazole
with an acid of formula XH, wherein XH denotes the respective conjugate acid of $X^-$.

The invention further relates to a compound of formula (II),

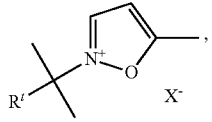
(II)

wherein $X^-$ denotes a group selected from among an anion selected from among $PF_6^-$, $BF_4^-$, $SbF_6^-$, phenylsulphonate, p-toluenesulphonate, $HSO_4^-$, $(SO_4^{2-})/2$, $FSO_3^-$ and $F_3CSO_3^-$ and $R^t$ denotes $C_{1-4}$-alkyl.

Preferred is a compound wherein $X^-$ denotes $PF_6^-$ and $R^t$ denotes methyl.

The invention further relates to the use of a compound of formula (II) for the preparation of acylguanidines and acylthioureas, preferably for the preparation of acylguanidines.

The invention further relates to the use of a compound of formula (II) for the preparation of carboxylic acid 2-(2-methyl-$C_{1-6}$-alk-2-yl)carbamoyl-1-methyl-vinyl esters, preferably for the preparation of a compound of formula (III).

The invention further relates to a compound of formula (III.1)

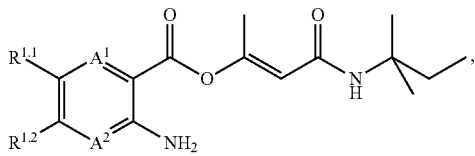
(III.1)

wherein $A^1$ and $A^2$ independently from each other denote N or CH;

$R^{1.1}$ denotes hydrogen or a group selected from among chloro, bromo and methyl, $R^{1.2}$ denotes hydrogen or a group selected from among amino, $C_{1-3}$-alkyl-NH—, $(C_{1-3}$-alkyl$)_2$N— and methyl, or $R^{1.1}$ and $R^{1.2}$ together form an annelated benzo ring.

Preferred is a compound of formula (III.2)

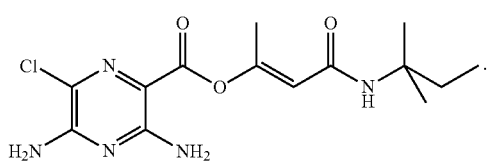
(III.2)

The invention further relates to the use of a compound of formula (III.2) for the preparation of a compound of formula (I.1)

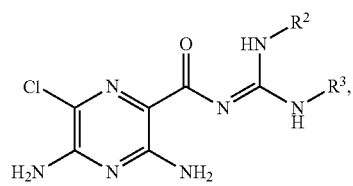
(I.1)

wherein $R^2$ denotes hydrogen or a group selected from among $C_{1-6}$-alkyl, $C_{6-10}$-aryl-$C_{1-6}$-alkyl-, heterocyclyl and heterocyclyl-$CH_2$;

or $R^2$ denotes a group of formula (ii) including the pure enantiomers thereof

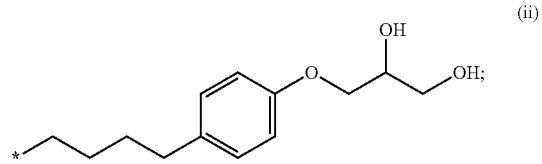 [SMILES: *CCCCc1ccc(OCC(O)CO)cc1]
(ii)

or $R^2$ denotes a group of formula (iii)

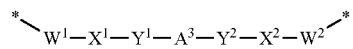
(iii)

wherein $W^1$ and $W^2$ are independently selected from among a bond or $C_{1-8}$-alkylene;

$X^1$ and $X^2$ are independently selected from among a 4- to 14-membered heterocyclic group;

$Y^1$ and $Y^2$ are independently selected from among a bond, $C_{1-8}$-alkylene- or —$C_{1-8}$-alkylamino-;

$A^3$ is selected from the group consisting of a $C_{6-15}$-membered aromatic carbocyclic group, —CONR$^5$—($C_{1-8}$-alkylene)-NR$^5$CO—, —CO—($C_{1-8}$-alkylene)-CO—, —CO—($C_{2-8}$-alkenylene)-CO—, —(CO)—, —CO—($C_{1-8}$-alkylene)-Z—($C_{1-8}$-alkylene)-CO—, —CO—($C_{1-8}$-alkylene)-Z—CO—, —CO—Z—CO—, —CO—NR$^5$—($C_{1-8}$-alkylene)-Z—($C_{1-8}$-alkylene)-NR$^5$—CO—, —CO—NR$^5$—($C_{1-8}$-alkylene)-Z—NR$^5$—CO—, —CO—NR$^5$—Z—NR$^5$—CO—, $C_{3-15}$-carbocyclic group and a 4- to 14-membered heterocyclic group;

Z is selected from among $C_{6-15}$-membered aromatic carbocyclic group, $C_{3-15}$-carbocyclic group and a 4- to 14-membered heterocyclic group;

$R^5$ is hydrogen or $C_{1-8}$-alkyl;

$R^3$ denotes hydrogen or methyl or $R^2$ and $R^3$ together denote —$CH_2$—$CH_2$— or —$CH_2$—$CH_2$—$CH_2$—.

TERMS AND DEFINITIONS USED

The compounds according to the invention unless otherwise specified may be present in the form of the tautomers as well as in the form of the free bases or the corresponding acid addition salts with pharmaceutically acceptable acids—such as for example acid addition salts with hydrochloric acid, hydrobromic acid, sulphuric acid, methanesulphonic acid, phosphoric acid, fumaric acid, succinic acid, lactic acid, citric acid, tartaric acid, or maleic acid.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_{1-6}$-alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. (also see Pharmaceutical salts, Birge, S. M. et al., J. Pharm. Sci., (1977), 66, 1-19). As the compounds of the present invention may have both, acid as well as basic groups, those compounds may therefore be present as internal salts too.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

The term "aryl" as used herein, either alone or in combination with another substituent, means either an aromatic monocyclic system or aromatic multicyclic systems containing carbon atoms. For example, aryl includes a phenyl or a naphthyl ring system, wherein aryl means generally an aromatic system, for example phenyl.

The term "heteroaryl" (heterocyclic aromatic groups) denotes five- or six-membered heterocyclic aromatic groups or 5-10 membered, bicyclic heteroaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

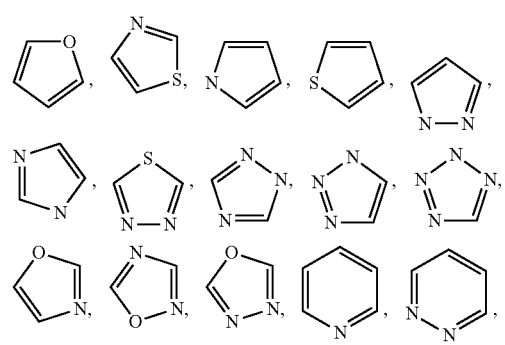

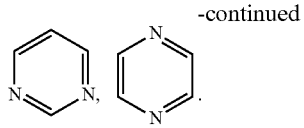

Examples of 5-10-membered bicyclic heteroaryl rings include pyrrolizine, indole, indolizine, isoindole, indazole, purine, quinoline, isoquinoline, benzimidazole, benzofuran, benzopyrane, benzothiazole, benzoisothiazole, pyridopyrimidine, pteridine and pyrimidopyrimidine.

The term "annelated species of aryl or heteroaryl" as used herein, either alone or in combination with another substituent wherein the annelated species presents as a aryl-het (a), a het-aryl (b) or a het-het (c) annelation means a monovalent substituent derived by removal of one hydrogen from
an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or
a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or
a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of an annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc. By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene also include all the possible isomeric forms of the relevant groups with the same number of carbons. Thus for example propyl also includes 1-methylethylene and butylene includes 1-methylpropylene, 1,1-dimethylethylene, 1,2-dimethylethylene.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Preferred are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the respective groups with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the respective groups. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Alkynylene groups with 2 to 4 carbon atoms are preferred. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the respective groups with the same number of carbons. Thus for example propynyl also includes 1-methylethynylene and butynylene includes 1-methylpropynylene, 1,1-dimethylethynylene, 1,2-dimethylethynylene.

By the term "$C_{1-6}$-alkoxy" (including those which are part of other groups) are meant branched and unbranched alkoxy groups with 1 to 6 carbon atoms and by the term "$C_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "$C_{3-8}$-cycloalkyl" (including those which are part of other groups) as used herein means cyclic alkyl groups with 3 to 8 carbon atoms, preferred are cyclic alkyl groups with 5 to 6 carbon atoms. Examples include: cyclopropyl, cyclobutyl, cyclopentyl, cyclohexyl, cycloheptyl or cyclooctyl.

By the term "$C_{3-6}$-cycloalkenyl" (including those which are part of other groups) is a cyclic alkyl group meant with 5 or 6 carbon atoms which contain one or two double bonds. Examples include: cyclopentenyl, cyclopentadienyl, cyclohexenyl or cyclohexadienyl.

By the term "$C_{1-6}$-haloalkyl" (including those which are part of other groups) are meant branched and unbranched alkyl groups with 1 to 6 carbon atoms wherein one or more hydrogen atoms are replaced by a halogen atom selected from among fluorine, chlorine or bromine, preferably fluorine and chlorine, particularly preferably fluorine. By the term "$C_{1-4}$-haloalkyl" are meant correspondingly branched and unbranched alkyl groups with 1 to 4 carbon atoms, wherein one or more hydrogen atoms are replaced analogously to what was stated above. $C_{1-4}$-haloalkyl is preferred. Examples include: $CH_2F$, $CHF_2$, $CF_3$.

Where a hyphen open on one side "-" is used in the structural formula of a substituent, this hyphen is to be understood as the linkage point to the remainder of the molecule. The substituent replaces the corresponding groups $R^1$, $R^2$, etc. If no hyphen open on one side is used in the structural formula of a substituent, the linkage point to the remainder of the molecule is clear from the structural formula itself.

Where a star "*" is used in the structural formula of a substituent, this star is to be understood as the linkage point to the remainder of the molecule. The substituent replaces the corresponding groups $R^1$, $R^2$, etc. If there are two stars used in the structural formula of a substituent the substituent is linked with two molecules.

The substituent $R^1$ denotes a group of formula (i),

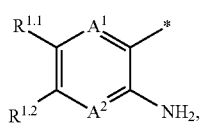

wherein
$A^1$ and $A^2$ independently from each other denote N or CH, preferably N;
$R^{1.1}$ denotes hydrogen or a group selected from among chloro, bromo and methyl, preferably chloro.
$R^{1.2}$ denotes hydrogen or a group selected from among amino, $C_{1-3}$-alkyl-NH—, $(C_{1-3}$-alkyl$)_2$N— and methyl, preferably amino.
or
$R^{1.1}$ and $R^{1.2}$ together form an annelated benzo ring;

The substituent $R^2$ denotes hydrogen or a group selected from among $C_{1-6}$-alkyl, $C_{6-10}$-aryl-$C_{1-6}$-alkyl-, heterocyclyl, heterocyclyl-$CH_2$—, -, preferably benzyl,
more preferably $R^2$ denotes a group of formula (ii)

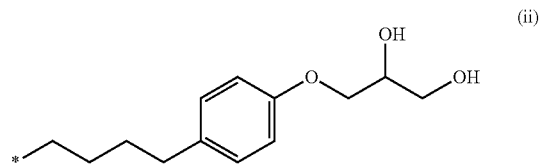 [SMILES: *CCCCc1ccc(OCC(O)CO)cc1]

including the pure enantiomers thereof,
or also preferred
$R^2$ denotes, with the provisio that $A^1$ and $A^2$ denote N, a group of formula (iii)

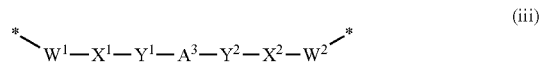

wherein
$W^1$ and $W^2$ are independently selected from among a bond or $C_{1-8}$-alkylene;
$X^1$ and $X^2$ are independently selected from among a 4- to 14-membered heterocyclic group;
$Y^1$ and $Y^2$ are independently selected from among a bond, $C_{1-8}$-alkylene- or —$C_{1-8}$-alkylamino-;
$A^3$ is selected from the group consisting of a $C_{6-15}$-membered aromatic carbocyclic group, —$CONR^5$— ($C_{1-8}$-alkylene)-$NR^5CO$—, —CO—($C_{1-8}$-alkylene)-CO—, —CO—($C_{2-8}$-alkenylene)-CO—, —(CO)—, —CO—($C_{1-8}$-alkylene)-Z—($C_{1-8}$-alkylene)-CO—, —CO—($C_{1-8}$-alkylene)-Z—CO—, —CO—Z—CO—, —CO—$NR^5$—($C_{1-8}$-alkylene)-Z—($C_{1-8}$-alkylene)-$NR^5$—CO—, —CO—$NR^5$—($C_{1-8}$-alkylene)-Z—$NR^5$—CO—, —CO—$NR^5$—Z—$NR^5$—CO—, $C_{3-15}$-carbocyclic group and a 4- to 14-membered heterocyclic group;
Z is selected from among $C_{6-15}$-membered aromatic carbocyclic group, $C_{3-15}$-carbocyclic group and a 4- to 14-membered heterocyclic group;
$R^5$ is hydrogen or $C_{1-8}$-alkyl;
$R^3$ denotes a hydrogen or methyl, preferably hydrogen or
$R^2$ and $R^3$ together denote —$CH_2$—$CH_2$— or —$CH_2$—$CH_2$—$CH_2$—, The substituent $R^4$ may denote a group selected from among alkylthio, 1-pyrazolyl, 1-imidazolyl and 1,2,4-triazol-1-yl, each optionally substituted by one or two methyl groups, preferably 1-pyrazolyl.

The substituent $R^t$ denotes a group selected from among $C_{1-4}$-alkyl, preferably methyl or ethyl.

$X^-$ denotes a group selected from among $PF_6^-$, $BF_4^-$, $SbF_6^-$, phenylsulphonate, p-toluenesulphonate, $HSO_4^-$, $(SO_4^{2-})/2$, $FSO_3^-$ and $F_3CSO_3^-$; preferably $PF_6^-$ and $F_3CSO_3^-$.

Process step (A) is preferably carried out neat or in a solvent selected from among water, methanol, ethanol, tetrahydrofuran (THF), diethylether, tert-butyl-methylether, dimethylformamide (DMF), N-methyl-2-pyrrolidone (NMP), N-ethyl-2-pyrrolidone (NEP) and dimethylsulphoxide (DMSO), or mixtures thereof, preferably in a mixture containing water and tetrahydrofuran (THF) and/or diethylether. Especially preferred is that all or part of the solvents used are added not from the beginning but after the addition of the acid XH in order to achieve precipitation of the compound (II) formed during the process.

Process step (A) is carried out in a temperature range of from −20° C. to 40° C., preferably from 0° C. to 25° C.

Process step (B) is preferably carried out in the presence of a base selected from among triethylamine, di-isopropyl-ethylamine and N-methylmorpholine, preferably triethylamine. Process step (B) is preferably carried out in a solvent selected from among DMF, NMP, NEP and DMSO, preferably in DMF.

Process step (B) is preferably carried out at an initial temperature ranging from 20° C. to 60° C., particularly preferably from 20° C. to 50° C. Preferably, the temperature is allowed to lower during the process, most preferably to ambient temperature. The skilled person will appreciate that depending on $R^1$, the addition of water at a later timepoint during the process may promote precipitation of the compound of formula (III) formed during the process. The final temperature when separating the product is preferably −20° C. to 25° C., most preferably 0° C. to 20° C.

Process step (C) is preferably carried out with the addition of a base selected from among triethylamine, di-isopropyl-ethylamine and N-methylmorpholine, preferably triethylamine. Process step (C) is preferably carried out neat or applying a solvent selected from among DMF NMP, NEP and DMSO, preferably DMF.

Stage 1 of process step (C) is preferably carried out in a temperature range of from 0° C. to 30° C., preferably from 0° C. to 20° C., particularly preferable at a temperature from 0° C. to 5° C. The skilled person will appreciate that depending on $R^1$, the addition of water at a later timepoint during the process may promote precipitation of the compound of formula (III) formed during the process. The final temperature when separating the product is preferably 0° C. to 25° C., most preferably 0° C. to 20° C.

Process step (D) is preferably carried out applying a base selected from among sodium hydroxide, sodium carbonate, sodium bicarbonate, potassium hydroxide, potassium carbonate, potassium tert-butylate, sodium methanolate and sodium ethanolate, preferably sodium hydroxide and potassium tert-butylate.

Process step (D) is preferably carried out applying a solvent selected from among tert-butylmethyl ether (TBME), tetrahydrofuran (THF), dichlormethane (DCM), acetonitrile, diethylether, dimethylformamide (DMF), N-methyl-2-pyrrolidone (NMP), N-ethyl-2-pyrrolidone (NEP) and dimethylsulphoxide (DMSO), or mixtures thereof, preferably TBME, THF and DCM, or a mixture thereof, particularly preferable TBME and THF or a mixture thereof. Process step (D) is preferably carried out in a temperature range of from 15° C. to the boiling point of the solvent applied. With the proviso that $R^4$ denotes alkylthio, process step (D) is most preferably carried out at a temperature from 15 to 25° C.

The skilled person will appreciate that depending on $R^3$ and $R^4$, the addition of water at a later timepoint during the process may promote precipitation of the compound of formula (IV) formed during the process.

Process step (E) is preferably carried out in the presence of a base selected from among sodium hydroxide, sodium carbonate, potassium hydroxide, potassium carbonate, sodium methanolate, sodium ethanolate and potassium tert-butanolate. Also preferred is the process step (E) carried out in the presence of an alcoholate generated by addition of sodium or sodium hydride to a solvent selected from methanol, ethanol, 2-propanol and tert-butanol. Most preferably, the process step is carried out in the presence of a base selected from among sodium hydroxide, potassium hydroxide, sodium ethanolate, sodium 2-propanolate, sodium tert-butanolate and potassium tert-butanolate which in the case of sodium alcoholates may be generated by addition of metallic sodium or sodium hydride to the respective alcohol.

In process step (E) formula (VIII) is preferably used as a free base or as an acid addition salt, preferably as an acid addition salt selected from among hydrochloric acid, hydrobromic acid, sulphuric acid, methylsulphonic acid and p-tolylsulphonic acid.

Process step (E) is preferably carried out in a solvent selected from among tetrahydrofuran (THF), dioxane, methanol, ethanol, 2-propanol and tert-butanol or a mixture thereof, most preferably in ethanol and 2-propanol.

Process step (E) is preferably carried out in a temperature range of from 40° C. to 90° C., preferably from 50° C. to 85° C.

Process step (F) is preferably carried out in the presence of a base selected from among triethylamine di-isopropyl-ethylamine and N-methylmorpholine, preferably triethylamine. Process step (F) is preferably carried out in a solvent selected from among methanol, ethanol, 2-propanol, acetonitrile, DCM, tetrahydrofuran (THF), diethylether, dimethylformamide (DMF), N-methyl-2-pyrrolidone (NMP), N-ethyl-2-pyrrolidone (NEP) and dimethylsulphoxide (DMSO), or mixtures thereof, preferably selected from among methanol, ethanol, DMF and THF or mixtures thereof, most preferably in ethanol and DMF.

Process step (F) is preferably carried out in a temperature range of from 50° C. to 90° C., preferably from 65° C. to 80° C.

Scheme 1 illustrates the synthesis according to the invention.

Scheme 1 Synthesis of Compounds of formula (I)

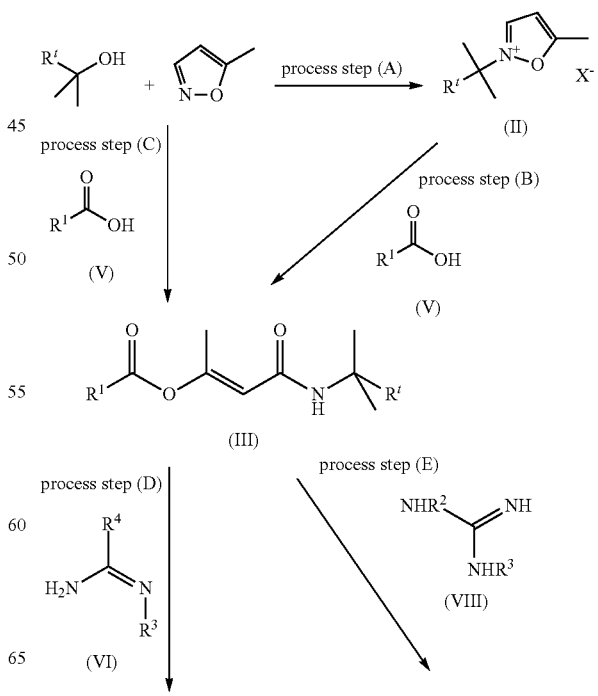

-continued process step (F)

(IV) + (VII) → (I)

The following examples serve to illustrate the process for preparing the compounds of formula (I) carried out by way of example. These examples are to be taken as an illustration of the invention without restricting the latter to its subject-matter.

Preparation of the Compounds According to Scheme 1

Example 1

2-tert-Butyl-5-methyl-1,2-oxazol-2-ium; hexafluoro-phosphate

Process Step (A)

To an ice-cold mixture of tert-butanol (11.4 g; 154 mmol) and 5-methylisoxazole (12.5 ml; 154 mmol) kept under nitrogen atmosphere is added dropwise with cooling (ice-bath) hexafluorophosphoric acid (60% in water; 22.7 ml; 154 mmol). The ice-bath is removed and the resulting mixture is stirred at r.t. for further 2 h. To the stirred mixture, THF (10 ml) and diethyl ether (40 ml) is added. After further stirring for 10 min, the precipitate formed is filtered off with suction, washed with diethyl ether and dried in vacuo ($C_8H_{14}NO \times F_6P$).

Yield: 19.6 g (45% of theory)

ESI Mass spectrum: m/z=140 [M]$^+$

IR (KBr): □=3159 (m), 1597 (s), 1513 (ss), 1381 (s), 1245 (s), 1212 (ss), 1053 (s), 1036 (s), 1008 (s), 813 (ss)

$^1$H-NMR (400 MHz, DMSO): δ=1.69 (s, 9H); 2.69 (s, 3H); 7.19 (s, 1H); 9.69 (s, 1H)

Melting point: 107-108° C.

Differential Scanning calorimetry data (Closed gold vessel):

Exothermic event of ΔH=656 J/g and $T_{onset}$=193° C.

For comparison:

Differential Scanning calorimetry data (Closed gold vessel) for 2-tert-butyl-5-methyl-1,2-oxazol-2-ium perchlorate ("Woodward's reagent L"):

Exothermic event of ΔH=4395 J/g and $T_{onset}$=158° C.

Example 2

1-(tert-Butylcarbamoyl)prop-1-en-2-yl 3,5-diamino-6-chloropyrazine-2-carboxylate Alternative 1 Via Process Step (B)

3,5-Diamino-6-chloropyrazine-2-carboxylic acid (2.00 g; 10.6 mmol) in abs. DMF (20.0 ml) is warmed to approx. 40-50° C. to achieve complete solution. 2-tert-butyl-5-methyl-1,2-oxazol-2-ium hexafluoro-phosphate (6.05 g; 21.2 mmol) and triethylamine (2.94 ml; 21.2 mmol) are added and the resulting mixture is stirred at r.t. over night. Ice-water is added and the precipitate formed is filtered off with suction, washed with water and dried in vacuo at 65° C. to yield the title compound ($C_{13}H_{18}ClN_5O_3$).

Yield: 2.76 g (79% of theory)

ESI Mass spectrum: m/z=328 [M+H]$^+$; m/z=326 [M−H]$^-$

Alternative 2 Via Process Step (C)

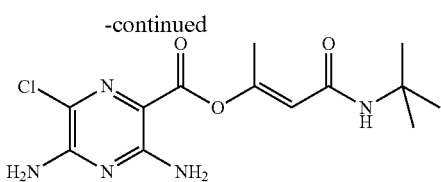

Stage 1:

A mixture of tert-butanol (21.0 ml; 226 mmol) and 5-methylisoxazole (18.0 ml; 221 mmol) is cooled with an ice-bath. Trifluoromethanesulphonic acid (20.0 ml; 221 mmol) is added dropwise with continued cooling. The resulting mixture is stirred for 1 h without further cooling.

Stage 2:

To a solution or suspension of 3,5-diamino-6-chloropyrazine-2-carboxylic acid (14.0 g; 74.2 mmol) and triethylamine (31.0 ml; 222 mmol) in DMF (1400 ml) is added the mixture prepared in stage 1. The resulting mixture is stirred for 4 h at r.t. Ice-water is added with stirring. The precipitate formed is filtered off with suction, washed with water and dried at 65° C. to yield the title compound ($C_{13}H_{18}ClN_5O_3$).

Yield: 18.2 g (75% of theory)
TLC (Silica; DCM/MeOH 9:1): $R_f$=0.4
ESI Mass spectrum: m/z=328 [M+H]$^+$; m/z=326 [M−H]$^-$ Example 3

1-(tert-Butylcarbamoyl)prop-1-en-2-yl 3-amino-6-chloropyrazine-2-carboxylate

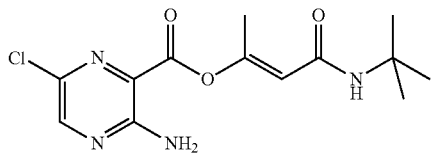 [SMILES: C/C(=C\C(=O)NC(C)(C)C)OC(=O)c1nc(Cl)cnc1N]

Process Step (B)

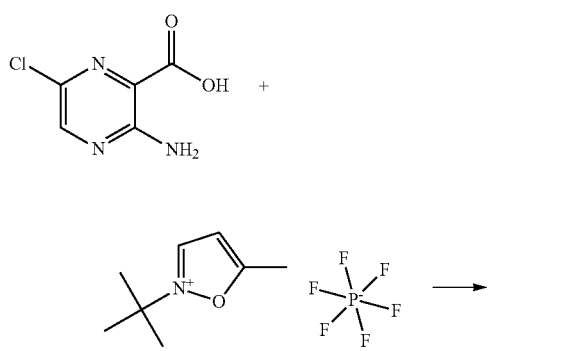

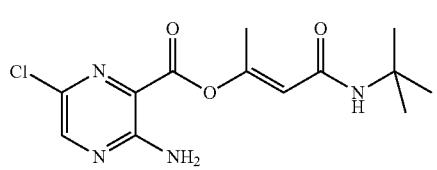

To a mixture of 3-amino-6-chloropyrazine-2-carboxylic acid (1.00 g; 5.76 mmol) and triethylamine (2.40 ml; 17.3 mmol) in abs. DMF is added 2-tert-butyl-5-methyl-1,2-oxazol-2-ium hexafluoro-phosphate (4.93 g; 17.3 mmol). The mixture is stirred at r.t. over night. Ice-water is added. The supernatant is decanted from the resin-like product which is sufficiently pure to be further reacted ($C_{13}H_{17}ClN_4O_3$)
ESI Mass spectrum: m/z=313 [M+H]$^+$ Example 4

1-(tert-Butylcarbamoyl)prop-1-en-2-yl 3-aminoquinoxaline-2-carboxylate

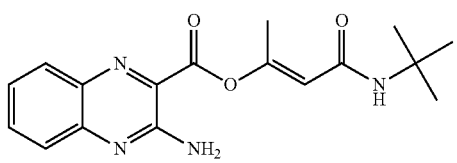 [SMILES: C/C(=C\C(=O)NC(C)(C)C)OC(=O)c1nc2ccccc2nc1N]

Process Step (C)

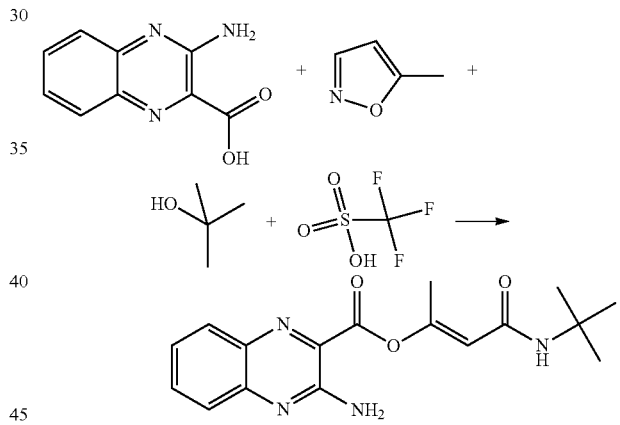

Stage 1:

A mixture of tert-butanol (7.06 g; 95.2 mmol) and 5-methylisoxazole (7.75 ml; 95.2 mmol) is cooled with an ice-bath. Trifluoromethanesulphonic acid (8.62 ml; 95.2 mmol) is added dropwise with continued cooling. The resulting mixture is stirred for 1 h without further cooling.

Stage 2:

A solution of 3-aminoquinoxaline-2-carboxylic acid (6.00 g; 31.7 mmol) in DMF (50.0 ml) and triethylamine (13.3 ml; 95.2 mmol) is added to the mixture prepared in stage 1 while cooling. The cooling bath is removed and the resulting mixture is stirred over night. Ice-water is added with stirring. The precipitate formed is filtered off with suction, washed with water and dried at 65° C. to yield the title compound ($C_{17}H_{20}N_4O_3$).

Yield: 10.2 g (98% of theory)
IR: 1715 cm$^{-1}$ (C=O ester); 1647 cm$^{-1}$ (C=O amide)
ESI Mass spectrum: m/z=329 [M+H]$^+$

Example 5

1-(tert-Butylcarbamoyl)prop-1-en-2-yl 3-amino-6-chloro-5-[(cyclopropylmethyl)amino]pyrazine-2-carboxylate

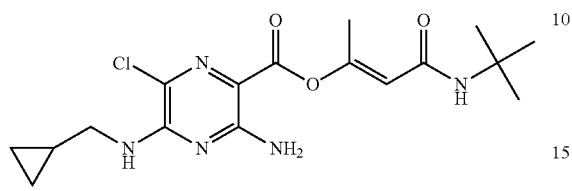

Process Step (C)

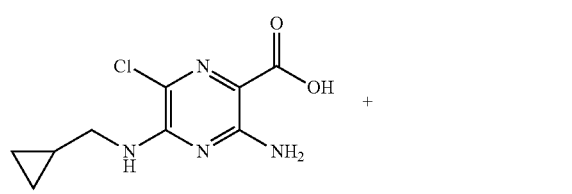

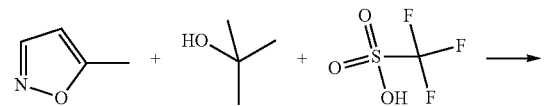

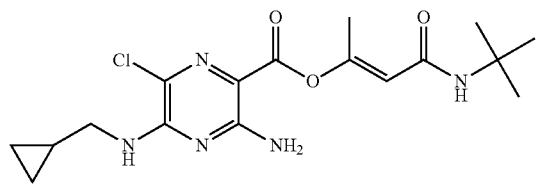 [SMILES: C/C(=C\C(=O)NC(C)(C)C)OC(=O)c1nc(Cl)c(NCC2CC2)nc1N]

Stage 1:

A mixture of tert-butanol (1.38 g; 18.5 mmol) and 5-methylisoxazole (1.51 ml; 18.5 mmol) is cooled with an ice-bath. Trifluoromethanesulphonic acid (1.68 ml; 1.85 mmol) is added dropwise with continued cooling. The resulting mixture is stirred for 1 h without further cooling.

Stage 2:

A solution of 3-amino-6-chloro-5-[(cyclopropylmethyl)amino]pyrazine-2-carboxylic acid (Prepared from the respective methyl ester by refluxing in aq. NaOH [J. Med. Chem. 10 (1967) 66-74]; 1.50 g; 6.18 mmol) in DMF (10.0 ml) and triethylamine (2.59 ml; 18.5 mmol) is added to the mixture prepared in stage 1 while cooling. The cooling bath is removed and the resulting mixture is stirred over night. Ice-water is added with stirring. The precipitate formed is filtered off with suction, washed with water and dried at 65° C. to yield the title compound ($C_{17}H_{24}ClN_5O_3$).

Yield: 2.31 g (98% of theory)

ESI Mass spectrum: m/z=382 [M+H]$^+$

Example 6

1-(2-Methyl-2-butyl-carbamoyl)prop-1-en-2-yl 3,5-diamino-6-chloropyrazine-2-carboxylate

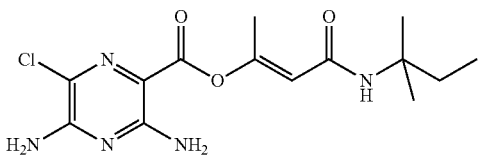 [SMILES: CCC(C)(C)NC(=O)/C=C(\C)OC(=O)c1nc(Cl)c(N)nc1N]

Process Step (C)

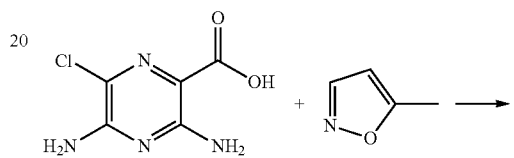

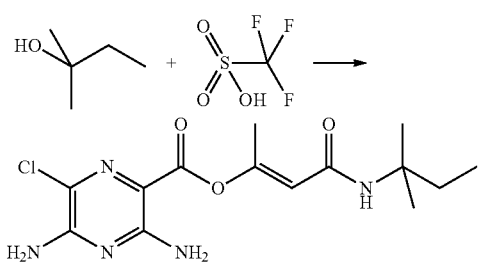

Stage 1:

A mixture of 2-methyl-2-butanol (60.0 ml; 98%; 537 mmol) and 5-methylisoxazole (46.0 ml; 95%; 536 mmol) is cooled with an ice-bath. Trifluoromethanesulphonic acid (51.0 ml; 98%; 565 mmol) is added dropwise while stirring with continued cooling. The resulting mixture is stirred for 1 h, then over night without further cooling.

Stage 2:

To 3,5-diamino-6-chloropyrazine-2-carboxylic acid (42.3 g; 224 mmol) in DMF (338 ml) is added dropwise triethylamine (78.0 ml; 560 mmol) while cooling with an ice-bath. To the resulting mixture is added dropwise while cooling with an ice-bath the mixture generated as described in "stage 1". The temperature is thereby kept below 25° C. The mixture is stirred for further 2 hours without cooling and then poured into ice-water (1436 ml). The resulting suspension is stirred for 2 hours at ambient temperature. The precipitate is filtered off with suction, taken up in THF/water (1:4; 75 ml), filtered again with suction and washed with water. The product is dried in vacuo at 60° C. ($C_{14}H_{20}ClN_5O_3$).

Yield: 75.1 g (98% of theory)

TLC: $R_f$=0.30 (Silica; DCM/MeOH/HOAc=20:1:0.1)

ESI Mass spectrum: m/z=342 [M+H]$^+$; m/z=340 [M−H]$^-$ $^1$H-NMR (400 MHz, DMSO): δ=0.69 (t, 3H, J=7.4 Hz); 1.13 (s, 6H); 1.57 (quart., 2H, J=7.4 Hz); 1.97 (s, 3H); 5.62 (s, 1H); 7.00 (s, 1H); 7.15 (sb, 2H); 7.40 (sb)

Example 7

3,5-Diamino-6-chloro-N-[(methylsulfanyl)methanimidoyl]pyrazine-2-carboxamide

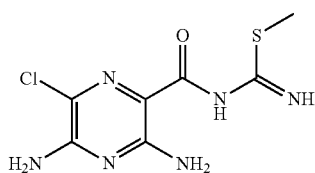

Process Step (D)

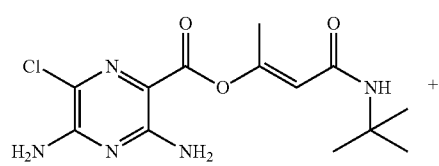

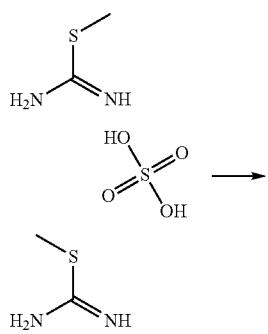

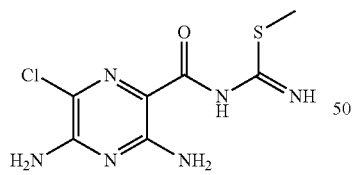

To NaOH (1 mol/l in water; 9.2 ml; 9.2 mmol) is added S-methylisothiourea sulphate (1.78 g; 6.1 mmol). The mixture is stirred until complete solution is achieved. TBME/THF (1:1; 30 ml) and then 1-(tert-butylcarbamoyl)prop-1-en-2-yl 3,5-diamino-6-chloropyrazine-2-carboxylate (example 2) (2.00 g; 6.10 mmol) are added and the mixture is stirred at r.t. over night, then water (6 ml) is added. The precipitate formed is filtered off with suction, washed successively with water, methanol and then with diethyl ether and then dried at 50° C. ($C_7H_9ClN_6OS$).

Yield: 1.33 g (84% of theory)

ESI Mass spectrum: m/z=261 [M+H]$^+$; m/z=259 [M−H]$^−$

Example 8

3-amino-N-[(methylsulfanyl)methanimidoyl]quinoxaline-2-carboxamide

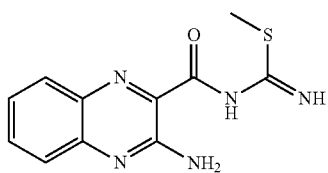

Process Step (D)

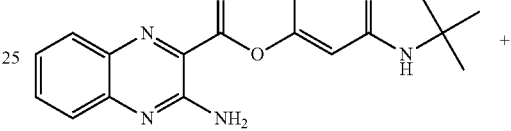

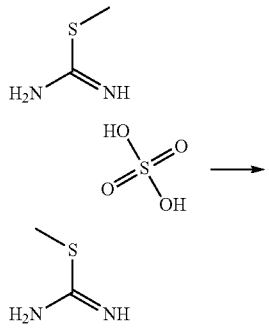

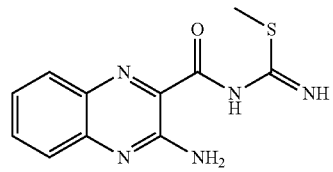 [SMILES: CSC(=N)NC(=O)c1nc2ccccc2nc1N]

To NaOH (1 mol/l in water; 45.7 ml; 45.7 mmol) is added S-methylisothiourea sulphate (10.6 g; 38.1 mmol). The mixture is stirred until complete solution is achieved. The resulting solution is added to a suspension of 1-(tert-butylcarbamoyl)prop-1-en-2-yl 3-aminoquinoxaline-2-carboxylate (example 4) (5.00 g; 15.2 mmol) in THF (80 ml). The mixture is stirred at r.t. for 3 h, then volatiles are evaporated. Ice-water (100 ml) is added. The precipitate formed is filtered off with suction, washed with water and then dried at 50° C. ($C_{11}H_{11}N_5OS$).

Yield: 2.95 g (74% of theory)

ESI Mass spectrum: m/z=262 [M+H]$^+$

HPLC analytics: RT=1.18 min (HPLC method 1)

Example 9

3-Amino-5-cyclopropylmethylamino-6-chloro-N-[(methylsulfanyl)methanimidoyl]pyrazine-2-carboxamide

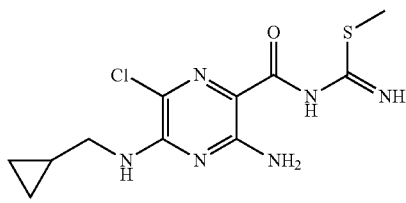 [SMILES: CSC(=N)NC(=O)c1nc(Cl)c(NCC2CC2)nc1N]

Process Step (D)

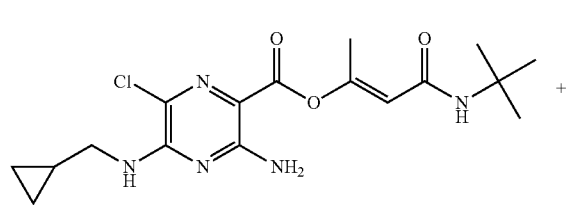

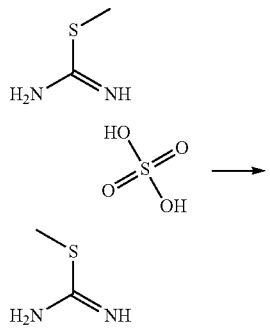

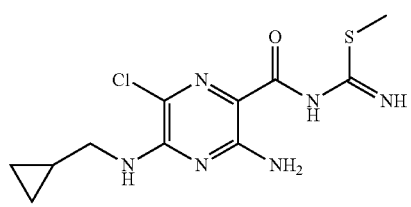

To NaOH (2 mol/l in water; 9.07 ml; 18.1 mmol) is added S-methylisothiourea sulphate (5.05 g; 18.1 mmol). The mixture is stirred until complete solution is achieved. The resulting solution is added to 1-(tert-butylcarbamoyl)prop-1-en-2-yl 3-amino-6-chloro-5-[(cyclopropylmethyl)amino]pyrazine-2-carboxylate (example 5) (2.31 g; 6.05 mmol) in THF (50 ml). The mixture is stirred at r.t. for 3 d, then volatiles are evaporated. The residue is purified by RP-HPLC (modifier: trifluoro acetic acid (TFA) ($C_{11}H_{15}ClN_6OS$).

Yield: 178 mg (9% of theory)

ESI Mass spectrum: m/z=315 [M+H]$^+$

Example 10

3,5-Diamino-6-chloro-N-[(1H-pyrazol-1-yl)methanimidoyl]pyrazine-2-carboxamide

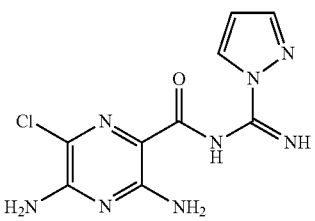

Process Step (D)

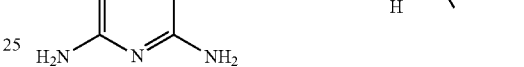

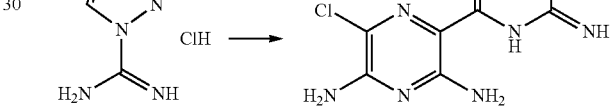

To a mixture of 1H-pyrazole-1-carboxamidine hydrochloride (238 mg; 99%; 1.61 mmol) and THF (2.0 ml) is added KOtBu (20% in THF; 1.00 ml; 1.61 mmol). A mixture of 1-(2-methyl-2-butylcarbamoyl)prop-1-en-2-yl 3,5-diamino-6-chloropyrazine-2-carboxylate (example 6) and THF (1.0 ml) is added with stirring. The mixture is refluxed over night, then allowed to cool to r.t. Water (6.0 ml) is added and the resulting suspension is stirred for 1 hour. The precipitate is filtered off with suction and washed successively with THF/water (1:2; 3 ml) and THF/water (1:3; 2.0 ml) ($C_9H_9ClN_8O$).

Yield: 260 mg (63% of theory)

TLC: $R_f$=0.45 (Silica; DCM/MeOH/aq. $NH_3$=9:1:0.1)

ESI Mass spectrum: m/z=281 [M+H]$^+$; m/z=279 [M−H]$^-$ $^1$H-NMR (400 MHz, DMSO+DCl): δ=6.96 (dd, J=3.0 Hz, J'=1.6 Hz, 1H); 8.28 (d, J=1.6 Hz, 1H); 9.26 (d, J=3.0 Hz, 1H)

Example 11

3,5-Diamino-N-[(1E)-amino(benzylamino)methylidene]-6-chloropyrazine-2-carboxamide

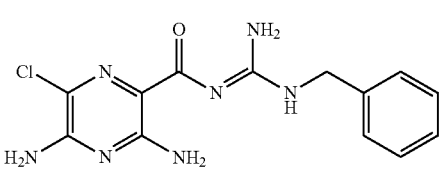 [SMILES: N/C(=N\C(=O)c1nc(Cl)c(N)nc1N)NCc1ccccc1]

Process Step (E)

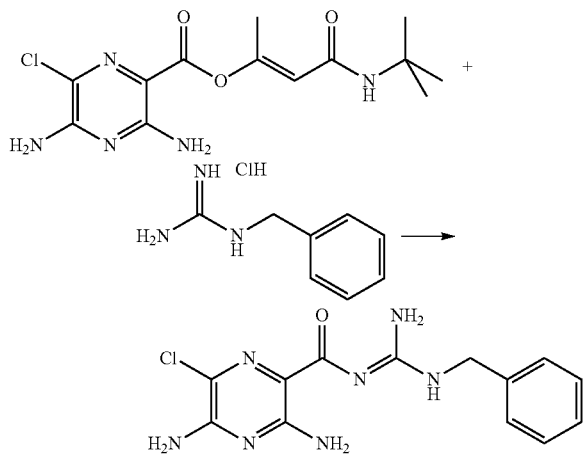

A mixture of benzylguanidine hydrochloride (113 mg; 610 µmol) and potassium tert-butylate (68 mg; 610 µmol) in dioxane (10 ml) is stirred at 50° C. for 30 min. 1-(tert-Butylcarbamoyl)prop-1-en-2-yl 3,5-diamino-6-chloropyrazine-2-carboxylate (example 2) (200 mg; 610 µmol) is added and the mixture is refluxed over night. Volatiles are evaporated and the residue is taken up in DMF. Insolubles are removed by filtration and the resulting solution is evaporated to dryness. The residue is purified by RP-HPLC (modifier: TFA) to yield the title compound as a TFA salt ($C_{13}H_{14}ClN_7O \times n$ TFA).

ESI Mass spectrum: m/z=320 [M+H]$^+$

Example 12

3,5-Diamino-6-chloro-N-(4,5-dihydro-1H-imidazol-2-yl)pyrazine-2-carboxamide

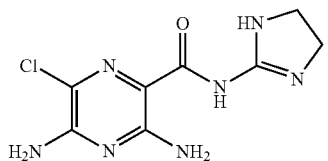 [SMILES: Nc1nc(N)c(C(=O)NC2=NCCN2)nc1Cl]

Process Step (E)

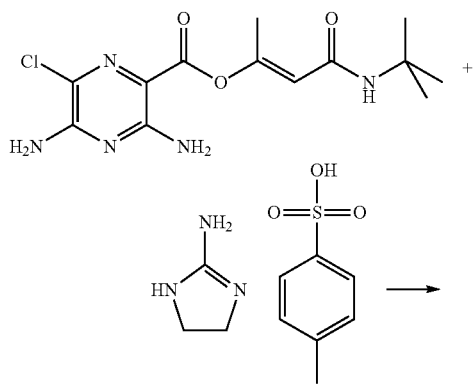

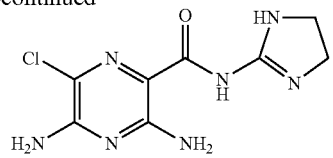

A mixture of 4,5-dihydro-1H-imidazol-2-ylamine tosylate (1.69 g; 6.57 mmol) and sodium (119 mg; 5.19 mmol) in 2-propanol (20 ml) is refluxed for 30 min. 1-(tert-Butylcarbamoyl)prop-1-en-2-yl 3,5-diamino-6-chloropyrazine-2-carboxylate (example 2) (0.900 g; 2.75 mmol) is added and the mixture is refluxed for further 60 min. The precipitate formed is filtered off with suction, suspended in water, filtered off again and dried at 50° C. to yield the title compound ($C_8H_{10}ClN_7O$).

Yield: 296 mg (42% of theory)

ESI Mass spectrum: m/z=256 [M+H]$^+$: m/z=254 [M–H]$^-$

HPLC analytics: RT=0.66 min (HPLC method 2)

Example 13

3,5-Diamino-N-[(1E)-amino({4-[4-(2,3-dihydroxypropoxy)phenyl]butyl}amino)methylidene]-6-chloropyrazine-2-carboxamide

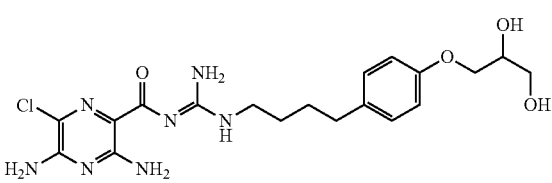 [SMILES: N/C(=N\C(=O)c1nc(Cl)c(N)nc1N)NCCCCc1ccc(OCC(O)CO)cc1]

Process Step (F)

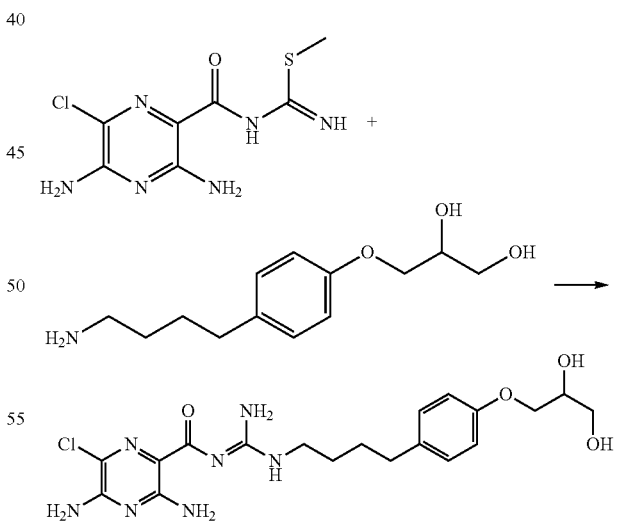

To a mixture of 3-[4-(4-aminobutyl)-phenoxy]propane-1,2-diol (prepared as described in J. Med. Chem. 49 (2006) 4098-4115; 530 mg; 2.22 mmol) and ethanol (2.0 ml) in THF (10.0 ml) are added triethylamine (1.23 ml; 8.86 mmol) and 3,5-diamino-6-chloro-N-[(methylsulfanyl)methanimidoyl]pyrazine-2-carboxamide (example 7; 577 mg; 2.22 mmol). The mixture is stirred at 70° C. over night, then volatiles are evaporated. The residue is purified by silica gel column chromatography (gradient: DCM/(Methanol/aq. ammonia 9:1) 95:5→70:30) to yield the title compound (C$_{19}$H$_{26}$ClN$_7$O$_4$).

Yield: 260 mg (26% of theory)

TLC (Silica; DCM/MeOH/aq. ammonia 70:30:1): R$_f$=0.3

ESI Mass spectrum: m/z=452 [M+H]$^+$; m/z=450 [M–H]$^-$

HPLC analytics: RT=1.40 min (HPLC method 1)

Example 14

3,5-Diamino-N-[(1E)-amino(benzylamino)methylidene]-6-chloropyrazine-2-carboxamide

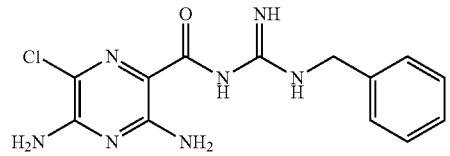 [SMILES: N=C(NCc1ccccc1)NC(=O)c1nc(Cl)c(N)nc1N]

Process Step (F)

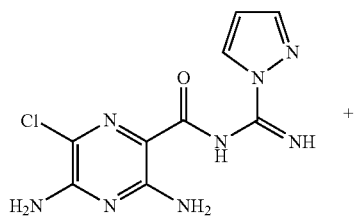

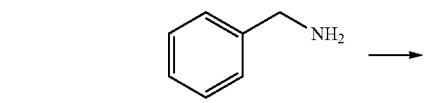

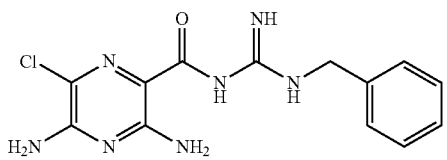

A mixture of 3,5-diamino-6-chloro-N-[(1H-pyrazol-1-yl)methanimidoyl]pyrazine-2-carboxamide (example 10) (250 mg; 0.891 mmol), benzylamine (0.120 ml; 1.10 mmol) and DMF (2.0 ml) is stirred at 70° C. for 6 h, then over night at r.t. Tert-butyl methyl ether (4.0 ml) is added and the mixture is stirred for further 2 hours. The precipitate is filtered off with suction, washed with tert-butyl methyl ether (4.0 ml) and dried in vacuo at 60° C. (C$_{13}$H$_{14}$ClN$_7$O).

Yield: 250 mg (73% of theory)

TLC: R$_f$=0.23 (Silica; DCM/MeOH/aq. NH$_3$=9:1:0.1)

ESI Mass spectrum: m/z=320 [M+H]$^+$; m/z=318 [M–H]$^-$

Example 15

1-(2-Methyl-2-butyl-carbamoyl)prop-1-en-2-yl-2-amino-5-bromobenzoate

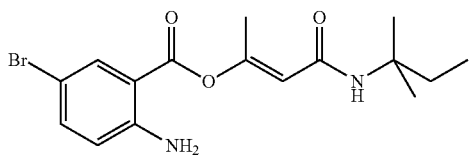 [SMILES: CCC(C)(C)NC(=O)/C=C(\C)OC(=O)c1cc(Br)ccc1N]

Process Step (C)

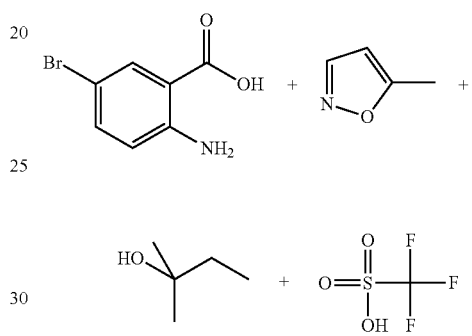

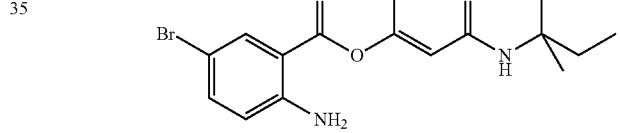

Stage 1:

A mixture of 2-methyl-2-butanol (1.34 ml; 98%; 12.0 mmol) and 5-methylisoxazole (1.03 ml; 95%; 12.0 mmol) is cooled with an ice-bath. Trifluoromethanesulphonic acid (1.13 ml; 98%; 12.5 mmol) is added dropwise while stirring with continued cooling. The resulting mixture is stirred for 1 h, then over night without further cooling.

Stage 2:

To 2-amino-5-bromobenzoic acid (1.08 g; 5.00 mmol) in DMF (10 ml) is added dropwise triethylamine (1.81 ml; 13.0 mmol) while cooling with an ice-bath. To the resulting mixture is added dropwise while cooling with an ice-bath the mixture generated as described in "stage 1". The temperature is thereby kept below 25° C. The mixture is stirred for 3 days without cooling and then ice-water (30 ml) is added with vigorous stirring. The aqueous layer is decanted, additional ice-water and DCM are added. The organic layer is separated and evaporated. The residue is purified by silica gel column chromatography (gradient: DCM/methanol 100:0→93:7) to yield the title compound (C$_{16}$H$_{21}$BrN$_2$O$_3$).

Yield: 880 mg (48% of theory).

ESI Mass spectrum: m/z=369 [M+H]$^+$; m/z=367 [M–H]$^-$

HPLC analytics: RT=0.98 min (HPLC method 3)

Example 16

2-Amino-5-bromo-N-(4,5-dihydro-1H-imidazol-2-yl)benzamide

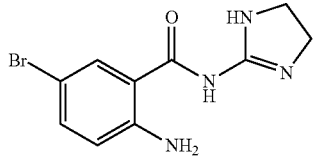 [SMILES: Nc1ccc(Br)cc1C(=O)NC1=NCCN1]

Process Step (E)

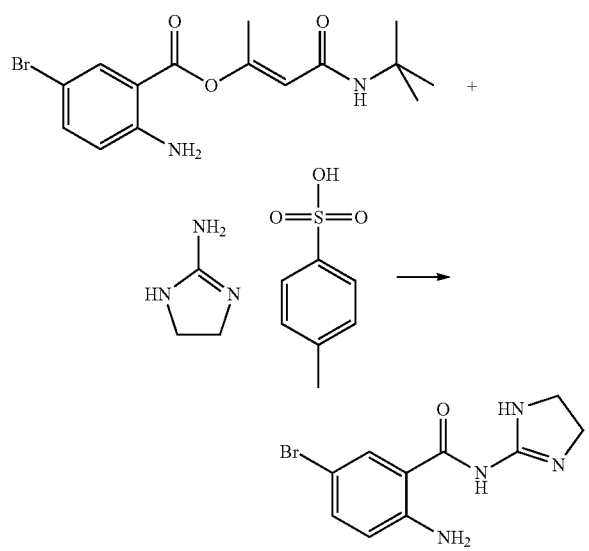

A mixture of 4,5-dihydro-1H-imidazol-2-ylamine tosylate (0.523 g; 2.03 mmol) and sodium (37 mg; 1.63 mmol) in 2-propanol (16 ml) is refluxed for 30 min. 1-(tert-Butylcarbamoyl)-prop-1-en-2-yl-2-amino-5-bromobenzoate (example 15) (0.300 g; 0.812 mmol) is added and the mixture is refluxed over night. The precipitate formed is filtered off and discarded. The filtrate is evaporated, and the residue is purified by preparative RP-HPLC (column: Xbridge C18 (Waters); water-ACN; modifier: ammonia) to yield the title compound ($C_{10}H_{11}BrN_4O$).

Yield: 96 mg (42% of theory)
ESI Mass spectrum: m/z=283 [M+H]$^+$; m/z=281 [M−H]$^−$
HPLC analytics: RT=0.68 min (HPLC method 4)

The following apparatus and test conditions are used to obtain the data presented above:
HPLC Analytics

HPLC method 1

| Column: | Sunfire C18, 4.6 × 30 mm, 2.5 µm | | | |
|---|---|---|---|---|
| Supplier: | Waters | | | |
| Gradient: time [min] | % Sol [H2O, 0.1% TFA] | % Sol [Methanol] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

HPLC method 2

| Column: | Sunfire C18, 3 × 30 mm, 2.5 µm | | | |
|---|---|---|---|---|
| Supplier: | Waters | | | |
| Gradient: time [min] | % Sol [H2O, 0.1% TFA] | % Sol [Methanol] | Flow [ml/min] | Temp [° C.] |
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

HPLC method 3

| Column: | Sunfire, 3 × 30 mm, 2.5 µm | | | |
|---|---|---|---|---|
| Supplier: | Waters | | | |
| Gradient: time [min] | % Sol [H2O, 0.1% TFA] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC method 4:

| Column: | Sunfire C18, 3 × 30 mm, 2.5 µm | | | |
|---|---|---|---|---|
| Supplier: | Waters | | | |
| Gradient: time [min] | % Sol H2O, 0.1% FA] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Infrared (IR) Spectroscopy
Solid material in KBr pellet. Peaks are given in cm$^{-1}$ and labelled, ss' (very strong), s' (strong), and, m' (medium).
Thin Layer Chromatography (TLC)
TLC silica glass plates from Merck are used (TLC Silica Gel 60F$_{254}$; 1.05729.0001).
The following abbreviations are used above and hereinafter:
ACN Acetonitrile
DCM Methylene chloride
DMF N,N-Dimethylformamide
ESI Electrospray ionization
FA Formic acid
RP-HPLC reversed phase high performance liquid chromatography
r.t. ambient temperature (e.g. 18 to 25° C., preferably 20° C.)
RT retention time
THF Tetrahydrofuran
TBME tert-Butylmethyl ether
TFA Trifluoroacetic acid
TLC Thin layer chromatography

| ACN | Acetonitrile |
|---|---|
| DCM | Methylene chloride |
| DMF | N,N-Dimethylformamide |
| ESI | Electrospray ionization |

-continued

| | |
|---|---|
| FA | Formic acid |
| RP-HPLC | reversed phase high performance liquid chromatography |
| r.t. | ambient temperature (e.g. 18 to 25° C., preferably 20° C.) |
| RT | retention time |
| THF | Tetrahydrofuran |
| TBME | tert-Butylmethyl ether |
| TFA | Trifluoroacetic acid |
| TLC | Thin layer chromatography |

The invention claimed is:

1. A process for the preparation of compounds of general formula (III) optionally in the form of a tautomer or acid addition salt thereof,
characterised in that the process comprises reaction step (C),
wherein
(C) is the reaction of a tertiary alcohol selected from tert-butanol, 2-methyl-2-butanol, 2-methyl-2-pentanol, 2-methyl-2-hexanol, 2,3-dimethyl-2-butanol or 2,4-dimethyl-2-pentanol;
and
5-methyl-1,2-oxazole
in the presence of an acid of formula XH
and a compound of formula (V)

$$R^1\text{—COOH} \qquad (V)$$

without isolation of a compound of formula (II)

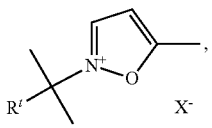

to form a compound of formula (III)

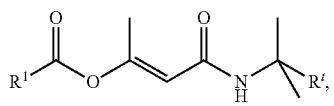

wherein
XH denotes an acid selected from among $HPF_6$, $HBF_4$, $HSbF_6$, phenylsulphonic acid, p-toluenesulphonic acid, $H_2SO_4$, $(H_2SO_4)/2$, $F_3CCOOH$, $FSO_3H$, or $F_3CSO_3H$;
$R^1$ denotes a group of formula (i),

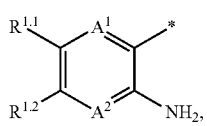

wherein
$A^1$ and $A^2$ independently from each other denote N or CH;
$R^{1.1}$ denotes a group selected from among hydrogen, chloro, bromo or methyl,
$R^{1.2}$ denotes a group selected from among hydrogen, amino, $C_{1-3}$-alkyl-NH—, $(C_{1-3}$-alkyl$)_2$N— or methyl,
or
$R^{1.1}$ and $R^{1.2}$ together form an annelated benzo ring; and
$R^t$ denotes $C_{1-4}$-alkyl.

2. The process according to claim 1 for the preparation of compounds of general formula (III),
wherein
$R^t$ denotes methyl or ethyl,
characterised in that the process comprises reaction step (C).

* * * * *